(12) United States Patent
Niessen et al.

(10) Patent No.: US 7,478,949 B2
(45) Date of Patent: Jan. 20, 2009

(54) X-RAY EXAMINATION APPARATUS AND METHOD

(75) Inventors: Wiro Joep Niessen, Utrecht (NL);
Everine Brenda Van De Kraats,
Utrecht (NL); Theo Van Walsum,
Utrecht (NL); Eeico Lennart Rommes,
Eindhoven (NL); Eugene Ivanov,
Eindhoven (NL); **Petrus Hubertus
Maria America**, Eindhoven (NL)

(73) Assignee: Koninklijke Philips Electronics N.V.,
Eindhoven (NL)

( * ) Notice: Subject to any disclaimer, the term of this patent is extended or adjusted under 35 U.S.C. 154(b) by 0 days.

(21) Appl. No.: 10/599,018

(22) PCT Filed: Mar. 11, 2005

(86) PCT No.: PCT/IB2005/050876
§ 371 (c)(1),
(2), (4) Date: Jun. 6, 2007

(87) PCT Pub. No.: WO2005/092196
PCT Pub. Date: Oct. 6, 2005

(65) Prior Publication Data
US 2007/0274450 A1 Nov. 29, 2007

(30) Foreign Application Priority Data
Mar. 23, 2004 (EP) .................................. 04101181

(51) Int. Cl.
*A61B 6/08* (2006.01)
(52) U.S. Cl. ........................................ 378/205; 378/197
(58) Field of Classification Search ......... 378/205–206, 378/207, 196–198, 62
See application file for complete search history.

(56) References Cited

U.S. PATENT DOCUMENTS

| | | | | |
|---|---|---|---|---|
| 6,470,207 B1* | 10/2002 | Simon et al. | ................. | 600/426 |
| 6,491,429 B1* | 12/2002 | Suhm | ......................... | 378/205 |
| 6,920,347 B2* | 7/2005 | Simon et al. | ................. | 600/424 |
| 2001/0036246 A1* | 11/2001 | Graumann | .................... | 378/39 |
| 2002/0099284 A1* | 7/2002 | Herrmann | .................... | 600/407 |
| 2003/0108154 A1* | 6/2003 | Schmitt | ...................... | 378/115 |
| 2003/0179856 A1* | 9/2003 | Mitschke et al. | ............ | 378/205 |
| 2004/0105526 A1* | 6/2004 | Zhang et al. | ................. | 378/205 |
| 2004/0111024 A1* | 6/2004 | Zheng et al. | ................. | 600/426 |

* cited by examiner

Primary Examiner—Hoon Song

(57) ABSTRACT

The present invention relates to an X-ray examination apparatus and a corresponding method for acquiring X-ray image data of a region of interest by use of an imaging unit (1-3) comprising an X-ray source (2) for emitting X-ray radiation and an X-ray detector (3) for detecting X-ray radiation after penetration of said region of interest. In order to provide a quick and easy method which also reduces the X-ray dose to which a patient is exposed and which allows immediate acquisition of X-ray image data from a desired and possibly optimal position, it is proposed that the X-ray examination apparatus according to the invention comprises further: processing means (22) for determining a desired position of said imaging unit (1-3), at which X-ray image data shall be acquired, based on a predetermined image acquisition plan (P) and/or an actual position (D) of an instrument (11), control means (23) for determining position parameters of said imaging unit (1-3) for said desired position, and positioning means (30) for positioning said imaging unit (1-3) at said desired position by use of said position parameters.

20 Claims, 3 Drawing Sheets

X-RAY EXAMINATION APPARATUS AND METHOD

Figure 1:
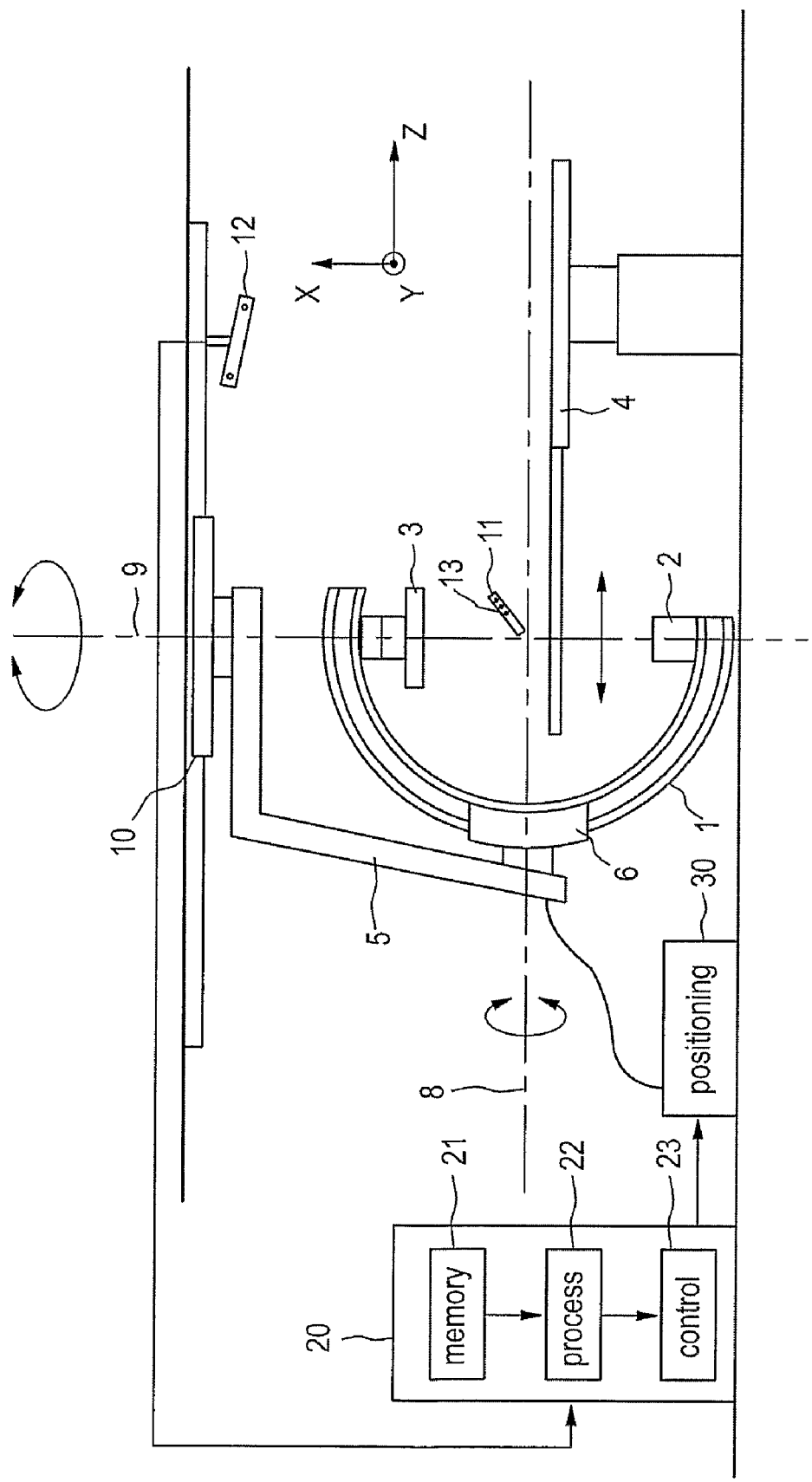

The present invention relates to an X-ray examination apparatus and a corresponding method for acquiring X-ray image data of a region of interest by use of an imaging unit comprising an X-ray source for emitting X-ray radiation and an X-ray detector for detecting X-ray radiation after penetration of said region of interest.

In cardiac care, a trend can be seen towards using less-invasive modalities, such as ultrasound, MR or CT, for diagnostic purposes before the patient is subjected to an X-ray treatment. Currently, the clinician manually maneuvers the imaging unit of an X-ray examining apparatus, in particular the C-arm on which the X-ray source and X-ray detector are mounted, to the desired position for acquiring X-ray image data. This can be cumbersome since it may require a large amount of time and leads to a large X-ray dose to the patient since X-ray image data are usually also acquired during the finding of the optimal position.

U.S. Pat. No. 6,491,429 discloses a method of automatic guiding a C-arm X-ray device which is equipped with a motorized positioning unit. By use of a navigation system the C-arm can be guided to a new position determined from a deviation between an actual position of a reference element and a previous position using automatic control. Initially, the optimal position of the C-arm with respect to the surgical scene in particular a bone, is manually obtained. If the position of the bone has changed by a surgical action, the position of the C-arm is corrected automatically.

It is an object of the present invention to provide an X-ray examination apparatus and a corresponding method by which the imaging unit can be automatically positioned at a desired position for acquiring X-ray image data so that the need for manually finding the desired position by acquiring X-ray image data during this finding can be avoided.

This object is achieved according to the present invention by an X-ray examination apparatus as claimed in claim 1 which, besides the imaging unit, comprises:

processing means for determining a desired position of said imaging unit, at which X-ray image data shall be acquired, based on a predetermined image acquisition plan and/or an actual position of an instrument, control means for determining position parameters of said imaging unit for said desired position, and positioning means for positioning said imaging unit at said desired position by use of said position parameters.

A corresponding X-ray examination method is defined in claim 9 which comprises the steps of:

determining a desired position of said imaging unit, at which X-ray image data shall be acquired, based on a predetermined image acquisition plan and/or an actual position of an instrument, determining position parameters of said imaging unit for said desired position, positioning said imaging unit at said desired position by use of said position parameters, and acquiring X-ray image data of said region of interest at said desired position.

The invention is based on the idea to use either a predetermined image acquisition plan and/or an actual position of an instrument, in particular a medical instrument, for determining position parameters of the desired position, for instance a position at which an optimal view of the desired object of interest can be obtained by use of the imaging unit used. For instance, when desiring to obtain an optimal view of a patient's blood vessel problem, it is quite often not immediately clear which is the optimal position of the imaging unit. When the optimal position parameters are found the imaging unit can then be positioned, preferably automatically by use a motorized imaging unit, at the desired position so that the X-ray image data can be obtained subsequently.

The invention thus provides an easy and fast method for obtaining X-ray image data at a desired position which generally also leads to a reduction of the X-ray dose to which a patient is subjected. Compared to the method disclosed in U.S. Pat. No. 6,491,429 it is not required according to the invention that initially the optimal position of the imaging unit with respect to the surgical scene is manually obtained. Further, no reference element is generally needed for determining any deviation between the reference element and the object of interest which may lead to a correction of the image unit's position.

Preferred embodiments of the invention are defined in the dependent claims. As mentioned, the positioning means preferably comprises automatic position control means for automatically positioning the imaging unit at the desired position. Thus, preferably, a motorized imaging unit is used which automatically moves the imaging unit at the desired position.

According to an alternative embodiment the positioning means comprises manual position control means for manually positioning the imaging unit at the desired position, a position check means for checking if the desired position has been reached, a signaling means for signaling if the desired position has been reached and/or how the desired position can be reached, and a tracking means for tracking the actual position of the imaging unit. The imaging unit is thus not positioned automatically, but manually by the operator. The operator will be notified by the signaling means when the desired position is reached. The actual position can be checked by a tracking means, for instance a common navigation system, and a position check means checks if the desired position has been reached. For instance, an acoustic or visual signal can be given to the operator when the desired position is reached. Another option is to visualize the line of imaging somehow, e.g. using a laser beam or a ray of light, in the intervention room which makes maneuvering to the desired position easier. Still a further option is to display the actual position schematically in an image in which also feedback can be given about the direction in which the imaging unit shall be moved to reach the desired position.

According to a further embodiment tracking means are provided for tracking the actual position of the instrument and the imaging unit, wherein the control means are operative for determining the position parameters by use of the tracked position of the instrument. Using a navigation system, e.g. having a camera that can track the position of the instrument and, possibly, also the position of the imaging unit, as tracking means, the instruments position can be determined easily, and planes through or perpendicular or, generally, related in any other way to the instrument can be provided to the imaging unit which can subsequently automatically (or manually) be moved to the desired position. From this position either a fluoroscopic image can be made or an X-ray plane can be reconstructed using a number of fluoroscopic images in a desired angular range. The larger the range the better the image quality, and the more X-ray images are acquired the better the image quality.

Preferably, the predetermined image acquisition plan is determined based on image data of the region of interest, in particular based on pre-acquisitioned 3D image data, which are registered to the imaging unit. Generally, image data of any modality can be used. Often, 3D volume data which have been acquired earlier for diagnostic purposes can be used.

However, also 3D rotational angiography data, which have been (e.g. intra-operatively) acquired just before or during the actual X-ray image data shall be acquired, can be used for determining the image acquisition plan. For instance, by use of 3D volume rendering or maximum or minimum intensity projections from a certain view point, an impression can be given of how an X-ray image would look when acquired with a conventional X-ray imaging unit from a particular position. By changing the view point virtually by use of these 3D volume data, the optimal position or several desired positions for acquiring X-ray image data can be determined resulting in said predetermined image acquisition plan used for controlling the imaging unit subsequently.

Generally, the image acquisition plan can be determined automatically, for instance using automatic segmentation methods, on available image data. However, the image acquisition plan can also be determined manually. Registration of the image data to the mechanics of the imaging unit is required to enable the control of the imaging unit to the correct position.

In a further embodiment calibration means are provided for calibrating the imaging unit with the predetermined image acquisition plan and/or the instrument. The instrument is thus linked to the imaging unit in one case so that one position of the imaging unit relative to the instrument is known, i.e. a step of calibration has to be performed in advance, and also the mechanics of the imaging unit need to be known for the tracking means. In a further case the image acquisition plan is registered to the imaging unit as mentioned above.

As already mentioned, the desired position preferably determines a desired plan or projection to be visualized, in particular with respect to the instrument or with respect to pre-acquisitioned 3D image data. Planes through, parallel to or perpendicular to medical instruments are usually the most relevant planes during interventional procedures at which X-ray image data shall be acquired. Further, planes through and/or perpendicular to specific objects of interest are often to be visualized. Such planes can be reconstructed by tomosynthesis. The instrument then determines the bisector which determines the X-ray plane to be reconstructed of the angular range over which the X-ray images are acquired. By knowing the bisector, the start of a sequence, depending on the desired angular range, is also known. The acquired X-ray image itself can be a projection, for instance perpendicular or parallel to the instrument, and can be a single X-ray image or a fluoroscopic image.

Figure 2:
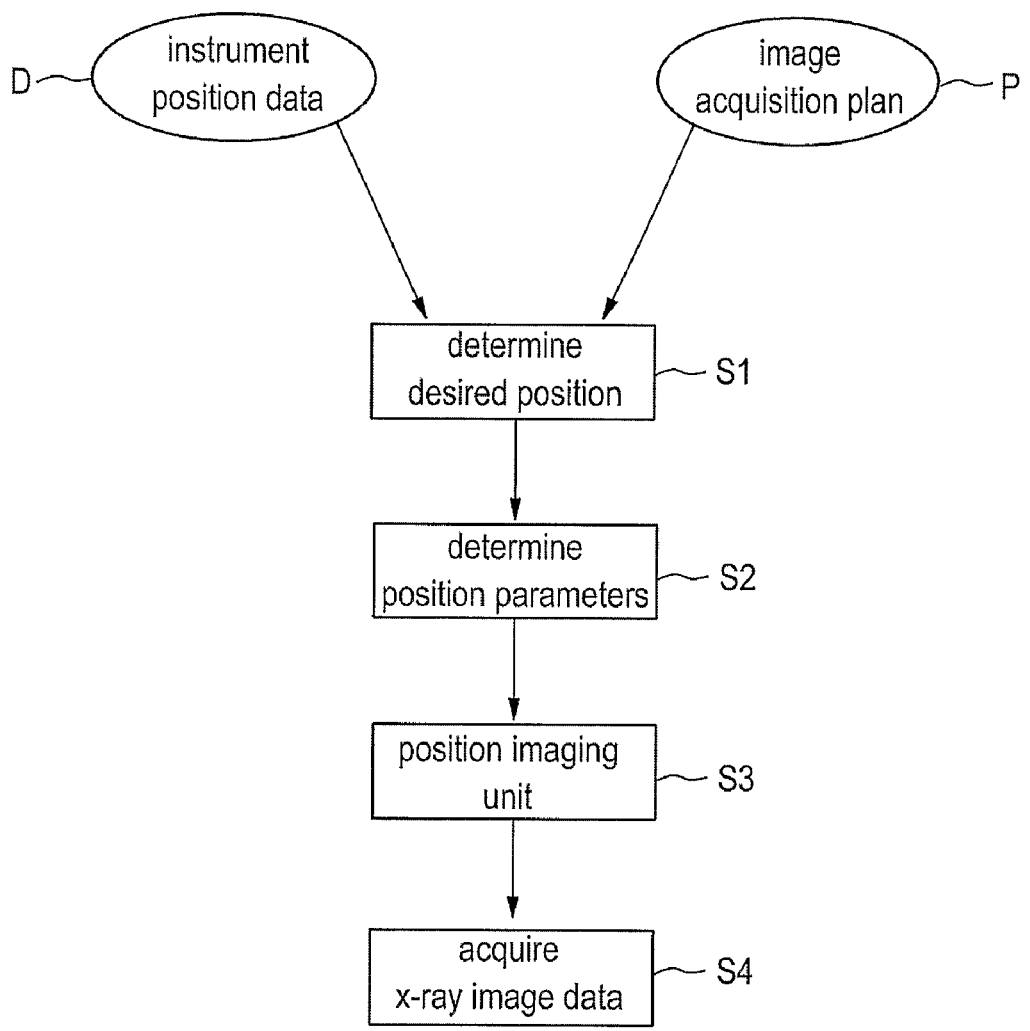
Figure 3:
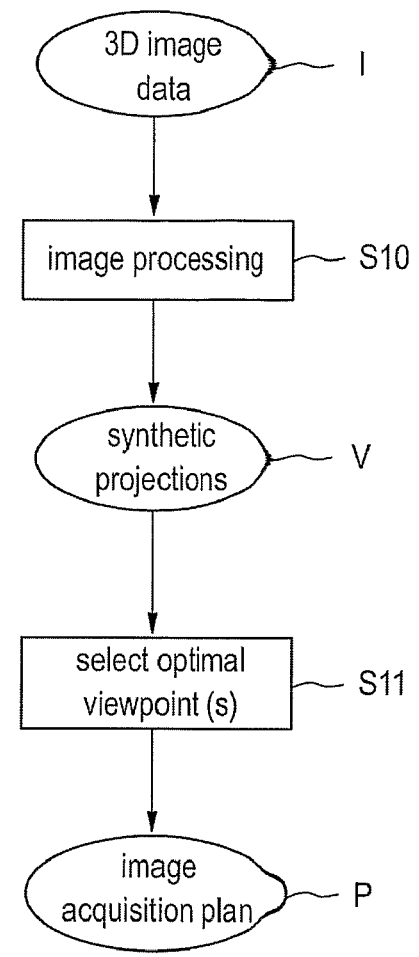
Figure 4:
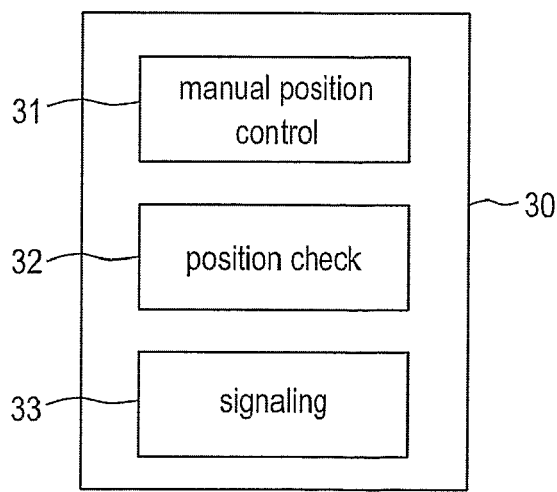

The invention will now be explained in more detail with reference to the drawings in which FIG. 1 shows an embodiment of an X-ray examination apparatus according to the invention, FIG. 2 shows a flow chart illustrating the X-ray examination method according to the invention, FIG. 3 shows a flow chart of a method for determining an image acquisition plan according to the invention and FIG. 4 shows an embodiment of a positioning unit according to the invention.

FIG. 1 shows an exemplary embodiment of an X-ray apparatus according to the present invention. In this embodiment a C-arm 1 is provided on which an X-ray source 2 and an X-ray detector 3 are mounted at the opposing ends of the C-arm 1 so that a region of interest of a patient lying on a patient table 4 can be subjected to X-ray radiation emitted by the X-ray source 2. The C-arm 1 is mounted to an L-arm 5 by a holding member 6 through which the C-arm can be rotated around a horizontal axis, in the shown position around the y-axis 7. Further, the C-arm 1 including the holding member 6 can be rotated around a second horizontal axis 8 perpendicular to the first horizontal axis 7, which second horizontal axis 8 corresponds to the z-axis in the position shown. The L-arm 5 is mounted to the ceiling in such a way that it can be rotated around a vertical axis 9 which corresponds to the x-axis in the position shown and which is perpendicular to the first and second horizontal axes 7 and 8. An additional translational movement of the L-arm is possible by use of guiding rails 10. Further details of the mechanical layout of such a C-arm X-ray examination apparatus are generally known and shall thus not be explained here.

For controlling the imaging unit comprising the C-arm including the X-ray source 2 and the X-ray detector 3 an image acquisition and control unit 20 is provided. Said unit 20 comprises a memory 21 for storing a predetermined image acquisition plan or pre-acquired image data for generating such a plan, a processing unit 22 for determining a desired position at which X-ray image data shall be acquired and a control unit 23 for determining position parameters of the imaging unit for said desired position. By use of a positioning unit 30 the imaging unit is then, preferably automatically, positioned at the desired position by use of such position parameters determined by the control unit 23.

The steps of this embodiment of the X-ray examination method according to the invention are again illustrated in FIG. 2. Therein, the steps S1 to S3 illustrate the determination of the desired position (S1) based on the given image acquisition plan P, the determination of the position parameters (S2) based on the desired position, and the positioning of the imaging unit (S3) based on these position parameters. Finally, in step S4, the X-ray image data are acquired at the desired position.

Alternatively to the image acquisition plan P the determination of the desired position can also be made using position data D of an instrument, in particular a medical instrument, such as a biopsy needle 11 schematically shown in FIG. 1. For obtaining the position of the medical instrument 11, preferably a tracking system is used including a camera system 12, for instance mounted on the ceiling and including two three-dimensional cameras tracking the position of the medical instrument 11 by use of appropriate markers 13 mounted on the instrument 11. Such a tracking system is generally known, and different embodiments, such as for instance using visible light, infrared light or other electromagnetic means for determining the position of the markers 13 are known and shall thus not be explained in more detail here. Any means that enable the determination of the three-dimensional position of the medical instrument 11 in space and/or with respect to the position of the imaging unit can generally be used.

The instrument's position data are then provided to the image acquisition and control unit 20 where they are used for determining the desired position of the imaging unit from which actual X-ray image data shall be acquired. It may, for instance, be desired that a plane through, perpendicular or parallel to the medical instrument shall be visualized in order to provide any details to the searching about the surrounding of the instrument's actual position. In this way, the positioning of the imaging unit can be directly coupled to any movement or change of the position of the medical instrument. It may be possible that the imaging unit immediately follows any change of the instrument's position. However, it may as well be possible that the position of the imaging unit is only changed upon a certain additional command in order to avoid a continuous movement of the imaging unit while the medical instrument is moved.

An embodiment of a method for determining the image acquisition plan is illustrated in FIG. 3. Therein, based on available image data I, preferably 3D image data of any modality, are used, which preferably have been acquired earlier for diagnostic purposes so that any additional image acquisition step is avoided. In an image processing step S10 one or more synthetic projections or any other two-dimensional viewmd V are determined which enable the finding of optimal viewing directions for the desired subsequent acquisition of X-ray image data. Such synthetic projections may be obtained by maximum or minimum intensity projections or by 3D volume rendering methods. Therefrom, one or more optimal view points are selected in step S11 which thus result in the desired image acquisition plan P. In this embodiment the image acquisition is determined manually on the original available 3D image data I. It is as well possible that the image acquisition plan P is determined automatically, for instance using automatic segmentation methods on the 3D image data I. Generally, it has to be ensured that the image data I or, at least, the image acquisition plan is registered, either directly or indirectly, to the mechanics of the imaging unit.

Preferably, the imaging unit is automatically positioned at the desired position. However, it is as well possible that the operator manually positions the imaging unit at the desired position. Therefore, as shown in FIG. 4, the positioning unit 30 comprises manual position control means 31 by which the operator can manually change the position of the imaging unit, e.g. fully manually or by motorized means which are controlled manually. Further, position check means 32 are provided which check if the desired position of the imaging unit has already been reached. For this purpose the tracking means described above for tracking the position of the medical instrument 11 can be used similarly for tracking the position of the imaging unit. In this case markers are provided on the C-arm, the X-ray source 2 and/or the X-ray detector 3 so that the position of the imaging unit in space can be determined.

Furthermore, signaling means 33 are provided by which it can be signaled to the operator if the desired position has already been reached or into which direction the imaging unit has to be maneuvered to reach the desired position. It is preferred that once the image acquisition plan is registered to the imaging unit, the object of interest should be tracked to keep the image acquisition plan up to date for the intraoperative situation. Furthermore, since the position of the plane with respect to the instrument is generally not fixed or well defined, infinite numbers of planes are parallel or perpendicular, or even in any other way related to the instrument. It is thus possible to use a special medical instrument having a reference plate which determines the desired plane.

Since generally the motorized imaging unit, for instance a C-arm, is limited in its movement and can thus not make all desired perspective projections or construct all desired planes, the constructional and mechanical limitations of the imaging unit should be known to the image acquisition and control unit. Thus, the plane or projection that is closest to the desired position should be determined in case, the actual desired position can not be used due to constructional or mechanical limitations of the imaging unit.

Generally, a calibration between instrument and imaging unit is necessary. A simple method for obtaining such a calibration uses a tracker plate attached to the base of the imaging unit or, for instance, to the ceiling if the X-ray examination unit is a fixed system.

It should be clear that the above described embodiment is just an example of a system where the invention can be used. The invention is, however, not limited to the use in such a C-arm X-ray apparatus, but can be generally applied in any kind of X-ray examination apparatus.

The invention claimed is:

1. X-ray examination apparatus for acquiring X-ray image data of a region of interest, comprising:
    an imaging unit comprising an X-ray source for emitting X-ray radiation and an X-ray detector for detecting X-ray radiation after penetration of said region of interest,
    a processing device for determining a desired position of said imaging unit, at which X-ray image data shall be acquired, based on a predetermined image acquisition plan and an actual position of an instrument, the predetermined image acquisition plan being associated with optimal viewing directions,
    a tracking device for tracking the actual position of said instrument and said imaging unit,
    a control device for determining position parameters of said imaging unit for said desired position, and
    a positioning device for positioning said imaging unit at said desired position by use of said position parameters.

2. X-ray examination apparatus as claimed in claim 1, wherein said positioning device comprises an automatic position control device for automatically positioning said imaging unit at said desired position.

3. X-ray examination apparatus as claimed in claim 1, wherein said positioning device comprises a manual position control device for manually positioning said imaging unit at said desired position, a position check device for checking if the desired position has been reached, and a signaling device for signaling if the desired position has been reached or a path to reach the desired position.

4. X-ray examination apparatus as claimed in claim 1, wherein said control device is operative for determining said position parameters by use of the tracked position of said instrument and wherein said position device moves said image device to said desired position in temporal proximity to said instrument being moved.

5. X-ray examination apparatus as claimed in claim 1, wherein said predetermined image acquisition plan is determined based on image data of said region of interest, wherein said image data is pre-acquisitioned 3D image data.

6. X-ray examination apparatus as claimed in claim 1, wherein said processing device comprise a calibration device for calibrating said imaging unit with said predetermined image acquisition plan and/or said instrument.

7. X-ray examination apparatus as claimed in claim 1, wherein said imaging unit further comprises a C-arm on which said X-ray source and said X-ray detector mounted.

8. X-ray examination apparatus as claimed in claim 1, wherein said desired position determines a desired plane or projection to be visualized with respect to said instrument or with respect to pre-acquisitioned 3D image data.

9. A method of X-ray examination for acquiring X-ray image data of a region of interest by use of an imaging unit comprising an X-ray source for emitting X-ray radiation and an X-ray detector for detecting X-ray radiation after penetration of said region of interest, comprising the steps of:
    determining a desired position of said imaging unit, at which X-ray image data shall be acquired, based on a predetermined image acquisition plan and an actual position of an instrument,
    tracking the actual position of the instrument and the imaging unit using a tracking device,
    determining position parameters of said imaging unit for said desired position,
    positioning said imaging unit at said desired position by use of said position parameters, and acquiring X-ray image data of said region of interest at said desired position.

10. The method of claim 9, further comprising calibrating said imaging unit with said predetermined image acquisition plan and said instrument.

11. The method of claim 9, further comprising manually positioning the imaging unit at the desired position.

12. The method of claim 11, further comprising:
determining if the desired position has been reached, and
signaling if the desired position has been reached.

13. The method of claim 9, further comprising providing information representative of how the desired position can be reached.

14. The method of claim 9, further comprising generating the predetermined image acquisition plan based on pre-acquired three dimensional data and synthetic projections.

15. X-ray examination apparatus for acquiring X-ray image data of a region of interest, comprising:
an imaging unit comprising an X-ray source for emitting X-ray radiation and an X-ray detector for detecting X-ray radiation after penetration of said region of interest,
a processing device for determining a desired position of said imaging unit, at which X-ray image data shall be acquired, based on a predetermined image acquisition plan and an actual position of an instrument,
a tracking device for tracking the actual position of said instrument,
a control device for determining position parameters of said imaging unit for said desired position, and
a positioning device for positioning said imaging unit at said desired position by use of said position parameters, wherein said positioning device comprises a manual position control device for manually positioning said imaging unit at said desired position.

16. The apparatus of claim 15, further comprising:
a position check device for checking if the desired position has been reached, and
a signaling device for signaling if the desired position has been reached.

17. The apparatus of claim 15, further comprising a calibrating device for calibrating said imaging unit with said predetermined image acquisition plan and said instrument, wherein said position device moves said image device to said desired position in temporal proximity to said instrument being moved.

18. The apparatus of claim 15, wherein the signaling device provides information representative of how the desired position can be reached.

19. The apparatus of claim 15, wherein the predetermined image acquisition plan is generated based on pre-acquired three dimensional data and synthetic projections.

20. The apparatus of claim 1, wherein the predetermined image acquisition plan is generated based on pre-acquired three dimensional data and synthetic projections.

* * * * *